(12) United States Patent
Lee et al.

(10) Patent No.: US 7,238,797 B2
(45) Date of Patent: Jul. 3, 2007

(54) NUCLEIC ACID ENCODING A PIG HEAT SHOCK PROTEIN 70

(75) Inventors: Wen-Chuan Lee, Miaoli Hsien (TW); Ming-Yu Chen, Miaoli Hsien (TW)

(73) Assignee: Animal Technology Institute, Miaoli Hsien (TW)

( * ) Notice: Subject to any disclaimer, the term of this patent is extended or adjusted under 35 U.S.C. 154(b) by 0 days.

(21) Appl. No.: 11/073,579

(22) Filed: Mar. 8, 2005

(65) Prior Publication Data

US 2005/0260746 A1 Nov. 24, 2005

Related U.S. Application Data

(60) Division of application No. 10/350,354, filed on Jan. 24, 2003, now Pat. No. 7,115,796, which is a continuation-in-part of application No. 10/138,317, filed on May 6, 2002, now abandoned.

(51) Int. Cl.
*C07H 21/02* (2006.01)
*C07H 21/04* (2006.01)
*A01K 67/027* (2006.01)

(52) U.S. Cl. .......................... 536/23.1; 800/13; 800/14; 800/17

(58) Field of Classification Search ...................... None
See application file for complete search history.

(56) References Cited

OTHER PUBLICATIONS

Peelman, LJ et al., Complete nucleotide sequence of a porcine HSP70 gene, Immunogenetics, 1992, 35:286-289.*
Chen, Ming-Yu, Partial Abstracts of the 5th Conference of the Asia-Pacific International Molecular Biology Network (A-IMBN)(Part I): Augmentation of thermotolerance in primary skin fibroblasts from a transgenic pig overexpressing the porcine HSP70.2, *Acta Biochimica et Biophysica Sinica* 35(2): 198, 2003.
Chen, Ming-Yu, "Augmentation of thermotolerance in primary skin fibroblasts from a transgenic pig overexpressing the porcine HSP70. 2", *Asian-Australia Journal of Animal Sciences*, 18(1): 107-112, 2005.
Kiang, J.G., et al., "Heat Shock Protein 70 kDa: Molecular Biology, Biochemistry, and Physiology" *Pharmacol. Ther.*, 1998, pp. 183-201, vol. 80, No. 2, Elsevier Science Inc., Washington, D.C.
Marber, M.S., et al., "Overexpression of the Rat Inducible 70-kD Heat Stress Protein in a Transgenic Mouse Increases the Resistance of the Heart to Ischemic Injury", *J. Clin. Invest*, Apr. 1995, pp. 1446-1456, vol. 95, The American Society for Clinical Investigation. Inc.
Mirkes, P.E., et al., "Heat Shock Protein 70 (Hsp70) Protects Postimplantation Murine Embryos From the Embryolethal Effects fo Hyperthermia" *Developmental Dynamics*, 1999, pp. 159-170, vol. 214, Wiley-Liss, Inc.
Plumier, J.C. et al., "Transgenic Mice Expressing the Human Heat Shock Protein 70 Have Improved Post-Ischemic Myocardial Recovery", *J. Clin. Invest.*, Apr. 1995, pp. 1854-1860, vol. 95, The American Society for Clinical Investigation. Inc.

* cited by examiner

*Primary Examiner*—Valarie Bertoglio
(74) *Attorney, Agent, or Firm*—Rothwell, Figg, Ernst & Manbeck PC

(57) ABSTRACT

The invention provides a transgenic pig having incorporated into its genome a HSP70 gene or fragment thereof, whereby the transgenic pig overexpresses HSP70. The transgenic pig of the invention can be used in the production of HSP in large quantities, as a xenograft source for transplation and as an animal model close to human for illustrating the protective roles of HSP. Furthermore, the transgenic pig of the invention has a better meat quality and exhibits an increased growth rate and a reduced backfat thickness.

2 Claims, 5 Drawing Sheets

NUCLEIC ACID ENCODING A PIG HEAT SHOCK PROTEIN 70

CROSS-REFERENCE TO RELATED APPLICATIONS

This application is a division of U.S. application Ser. No. 10/350,354, filed Jan. 24, 2003, now U.S. Pat. No. 7,115,796, which is a continuation-in-part of U.S. application Ser. No. 10/138,317, filed May 6, 2002, now abandoned.

BACKGROUND OF THE INVENTION

1. Field of the Invention

The present invention relates to a transgenic pig for overexpressing heat shock protein 70.

2. Description of the Prior Art

When exposed to nonlethal heat shock, a variety of organisms and cells acquire transient resistance to subsequent exposures to elevated temperatures. This phenomenon has been termed thermotolerance. Heat shock protein (hereafter HSP) 70 has been described as playing an important role in thermoresistance. HSP70 also is closely related to food intake, growth rate and backfat thickness of pigs. HSP is synthesized in cells in response to an increase of temperature above normal physiological levels, or following exposure to a variety of toxic agents. Recently, elevated expression of HSP70 and other HSPs has been observed in cells and tissues under conditions representative of human diseases, including ischemia, oxidant injury, immunology and infectious diseases (Marber, et al., 1995, *J. Clin. Invest.* 95:1446-1456 and Kiang et al., 1998, *Pharmacal. Ther.* 80:183-201). The increased expression of these stress proteins could represent an acute response to altered physiological states, as well as chronic adaption to some diseases. The primary function of these stress responses is thought to be cytoprotective. For example, overexpression of HSP70 alone was demonstrated to protect cells from thermal injury and to increase cell survival. By overexpressing rat inducible HSP70, postimplantation murine embryos were protected from heat treatment (Mirkes et al., 1999, *Developmental Dynamics,* 214:159-170). The protective role of HSP70 was demonstrated clearly by recent studies with transgenic mice in which overexpression of human or rat inducible HSP70 protected myocardium from ischemia reperfusion injury (Marber, et al., 1995, *J. Clin. Invest.* 95:1446-1456; and Plumier, et al., 1995, *J. Clin. Invest.,* 95:1854-1860).

Most studies concerning HSP70 were performed in vitro or in mice or rat models. However, since the in vitro model and the rat model are far from the human, they cannot be successfully applied in human. There is still a need to develop an animal model close to human for determining the effect of the HSP.

SUMMARY OF THE INVENTION

One object of the invention is to provide a transgenic pig having incorporated into its genome an HSP70 gene or fragment thereof, wherein said transgenic pig overexpresses HSP70.

A further object of the invention is to provide a transgene containing a pig HSP70 gene as shown in SEQ ID NO:1 or a fragment thereof and an expression vector containing the transgene.

DETAILED DESCRIPTION OF THE INVENTION

Figure 1:
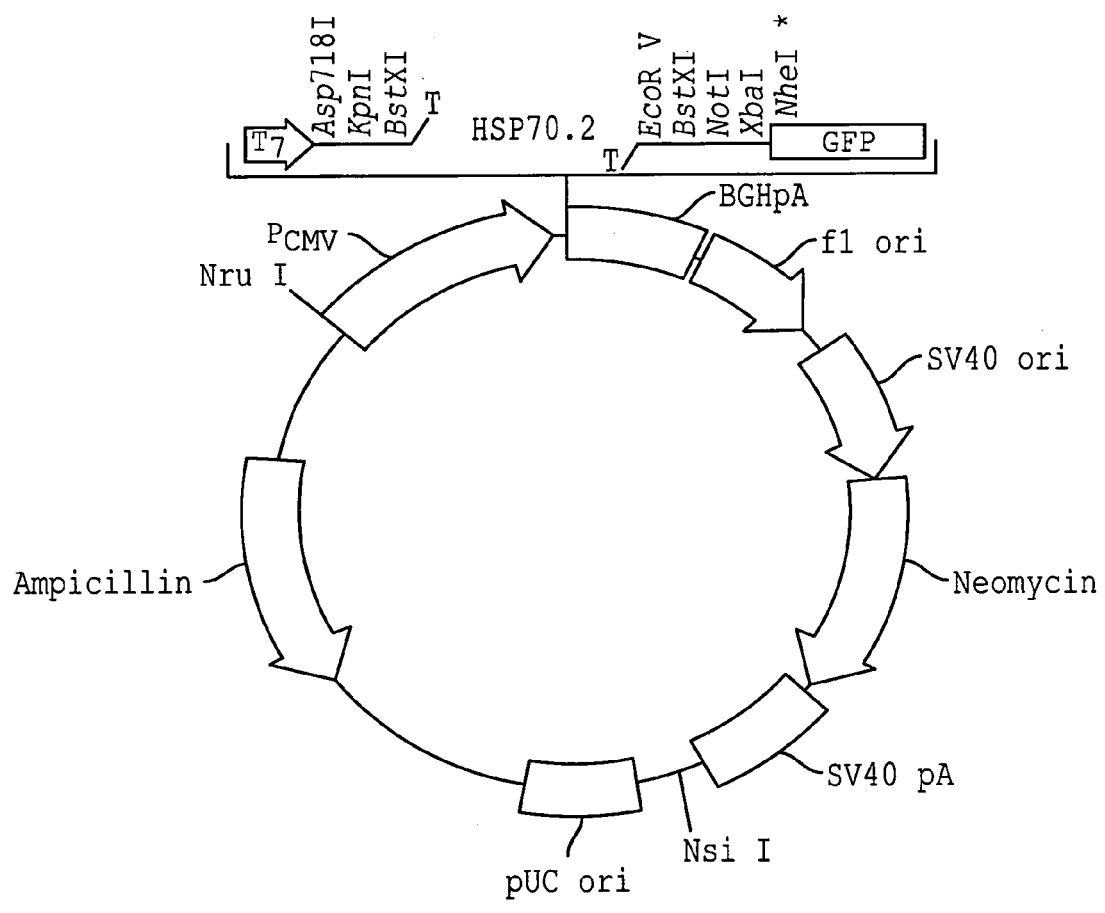
FIG. 1 shows the map of the hCMV/HSP70.2-GFP transgene.

The present invention features a transgenic pig having incorporated into its genome an HSP70 gene or fragment thereof. The invention successfully constructs transgenic pigs stably expressing an HSP70 gene. The transgenic pig of the invention can be used as an animal model close to human for realizing the protective roles and the clinical importance of HSP. Moreover, the transgenic pig of the invention provides an organ source for transplanting with low rejection.

Definitions

The term "heat shock protein 70 gene (HSP70 gene)," as used herein, refers to a multigene family with molecule masses of about 70 kDa. The HSP70 gene not only can be induced by heat but also amino acid analogs, glucose analogs, heavy metals, protein kinase C stimulators, Ca++-increasing agents, ischemia, sodium arsenite, microbial infections, nitric oxide, hormones and antibiotics.

The phrase "incorporated into its genome," as used herein, refers to pigs or other mammals which have a selected transgene introduced into their germ cells and/or somatic cells such that it is stably incorporated and is capable of carrying out a desired function.

The term "genome," as used herein, refers to the entire DNA complement of an organism, including the nuclear DNA component, chromosomal or extrachromosomal DNA, as well as the cytoplasmic domain (e.g., mitochondrial DNA).

The term "transgene," as used herein, refers to the introduction of a desired DNA sequence into the animal's genome, including but not limited to genes or DNA sequences which may not normally be present in the genome, genes which are present, but not normally transcribed and translated ("expressed") in a given genome, or any other genes or DNA sequences which one desires to introduce into the genome. This may include genes which may normally be present in the nontransgenic genome but which one desires to have altered in expression, or which one desires to introduce in an altered or variant form.

The term "expression vector," as used herein, refers to a vector capable of directing the expression of a gene to which it is operatively linked. In general, an expression vector of utility in recombinant DNA techniques is often in the form of a "plasmid" which refers generally to a circular double stranded DNA loop which, in its vector form, is not bound to the chromosome.

Transgene and Vector System

Transgenes are constructed for introducing into the germ line of an animal to make a transgenic pig. According to the invention, any suitable HSP70 gene can be incorporated into the genome of pigs. Preferably, said HSP70 gene is HSP70.2 gene. Preferably, said HSP70 gene is obtained from human or pig. More preferably, said HSP70 gene is selected from the group consisting of a pig HSP70.2 gene and a human HSP70.2 gene.

In one preferred embodiment of the invention, a new cloned pig HSP70 gene (SEQ ID NO:1) is incorporated into the genome of pigs. The new gene is cloned from pig testis cDNA and has 1923 nucleic acids.

TABLE I

Porcine HSP70.2 Gene Sequence.

(SEQ ID NO:1)

```
   1 ACAACTCCGC CCCATTGACG CAAATGGGCG GTAGGCGTGT ACGGTGGGAG

51 GTCTATATAA GCAGAGCTCT CTGGCTAACT AGAGAACCCA CTGCTTACTG

101 GCTTATCGAA ATTAATACGA CTCACTATAG GGAGACCCAA GCTGGCTAGT

151 TAAGCTTGGT ACCGAGCTCG GATCCACTAG TCCAGTGTGG TGGAATTGCC

201 CTTAACATGG CGAAGAGCGT GGCCATCGGC ATCGACCTGG GCACCACGTA

251 CTCGTGCGTG GGGGTGTTCC AGCACGGCAA GGTGGAGATC ATCGCCAACG

301 ACCAGGGCAA CCGCACTACC CCCAGCTACG TGGCCTTCAC GGACACCGAG

351 CGGCTGATCG GCGATGCGGC CAAGAACCAG GTGGCGCTGA ACCCGCAGAA

401 CACGGTGTTT GACGCGAAGC GGCTGATCGG GCGCAAGTTC GGCGACCCGG

451 TGGTGCAGGC GGACATGAAG CACTGGCCCT TCCGGGTGAT CAACGACGGG

501 GACAAGCCCA AGGTGCAGGT GAGCTACAAG GGCGAGACCA AGGCGTTCTA

551 CCCCGGAGGA GATCTCGTCGA TGGTGCTGAC CAAGATGAAG GAGATCGCCG

601 AGGCGTACCT GGGCCACCCG GTGAGCAACG CGGTGATCAC GGTGCCGGCC

651 TACTTCAACG ACTCGCAGCG GCAGGCCACC AAGGATGCGG GGGTGATCGC

701 GGGGCTGAAC GTGCTGCGGA TCATCAACGA GCCCACGGCG GCGGCCATCG

751 CCTACGGCCT GGACAGGACG GGCAAGGGGG AGCGCAACGT GCTGATCTTC

801 GACCTGGGCG GGGGCACGTT CGACGTGTCC ATCCTGACGA TCGACCACGG

851 CATCTTCGAG GTGAAGGCCA CGGCGGGGGA CACGCACCTG GGCGGCGAGG

901 ACTTCGACAA CAGGCTGGTG AACCACTTCG TGGAGGAGTT CAAGAGGAAG

951 CACAAGAAGG ACATCAGCCA GAACAAGCGG GCGGTGAGGC GGCTGCGCAC

1001 GGCCTGCGAG CGGGCCAAGA GGACCCTGTC GTCCAGCACG CAGGCCAGCC

1051 TGGAGATCGA CTCCCTGTTC GAGGGCATCG ACTTCTACAC GTCCATCACC

1101 CGGGCGCGCT TCGAGGAGCT GTGCTCGGAC CTGTTCCGCA GCACCCTGGA

1151 GCCGGTGGAG AAGGCTCTGC GCGACGCGAA GCTGGACAAG GGCCAGATTC

1201 ACGACCTGGT GCTGGTGGGG GGCTCGACGC GCATCCCCAA GGTGCAGAAG

1251 CTGCTGCAGG ACTTCTTCAA CGGGCGCGAC CTCAACAAGA GCATCAACCC

1301 GGACGAGGCG GTGGCGTATG GGGCGGCGGT GCAGGCGGCC ATCCTGATGG

1351 GCGACAAGTC GGAGAACGTG CAGGACCTGC TGCTGCTCGA CGTGGCCCCG

1401 CTGTCGCTGG GGCTGGAGAC GGCCGGCGGC GTGATGACGG CGCTGATCAA

1451 GCGCAACTCC ACCATCCCCA CCAAGCAGAC GCAGATCTTC ACCACGTACT

1501 CGGACAACCA GCCGGGCGTG CTGATCCAGG TGTACGAGGG CGAGAGGGCC

1551 ATGACGCGGG ACAACAACCT GCTGGGGCGC TTCGAGCTGA GCGGCATCCC

1601 GCCGGCCCCG CGGGGGGTGC CCCAGATCGA GGTGACCTTC GACATCGACG
```

TABLE I-continued

Porcine HSP70.2 Gene Sequence.

```
1651 CCAACGGCAT CCTGAACGTC ACGGCGACGG ACAAGAGCAC GGGCAAGGCC

1701 AACAAGATCA CCATCACCAA CGACAAGGGC CGGCTGAGCA AGGAGGAGAT

1751 CGAGCGCATG GTGCAGGAGG CGGAGAAGTA CAAAGCGGAG GACGAGATCC

1801 AGCGCGAGAG GGTGTCGGCC AAGAACGCGC TGGAGTCGTA CGCCTTCAAC

1851 ATGAAGAGCG CCGTGGAGGA TGAGGGGCTC AAGGGCAAGA TCAGCGAGGC

1901 GGACAAGAAG AAGGTGCTGG ACAAGTGTCA GGAGGTGATT TCCTGGCTGG

1951 ACGCCAACAC GCTGGCCGAG AAGGACGAGT TTGAGCACAA GAGGAAGGAG

2001 CTGGAGCAGG TGTGTAACCC CATCATCAGC GGACTGTACC AGGGGGCGGG

2051 TGGCCCCGGG GCTGGCGGCT TTGGGGCTCA GGCCCCCAAA GGGGGCTCTG

2101 GGTCTGGCCC CACCATCGAG GAGGTGGAAG GGCAATTCTG CAGATATCCA

2151 GCACAGTGGC GGCCGCTCGA GTCTAGAATG GCTAGCAAAG GAGAAGAACT

2201 TTTCACTGGA GTTGTCCCAA TTCTTGTTGA ATTAGATGGT GATGTTAATG

2251 GGCACAAATT TTCTGTCAGT GGAGAGGGTG AAGGTGATGC TACATACGGA

2301 AAGCTTACCC
```

According to the invention, any suitable vector system can be used to produce the transgenic HSP gene for being incorporated into the genome of pigs. Methods well known to those skilled in the art may be used to construct expression vectors containing the HSP gene and appropriate transcriptional and translational control elements. These methods include in vitro recombinant DNA techniques, synthetic techniques, and in vitro genetic recombination.

Trensgenic Pig

One object of the invention is to provide a transgenic pig having incorporated into its genome an HSP70 gene or fragment thereof, wherein said transgenic pig overexpresses HSP70.

According to the invention, transgenic pigs are produced by introducing transgenes into the germline of the pig. Embryonal target cells at various developmental stages can be used for introduction of transgenes. Different methods are used depending on the stage of development of the embryonal target cell. The specific line(s) of any animal used to practice this invention are selected for general good health, good embryo yields, good pronuclear visibility in the embryo, and good reproductive fitness.

Introduction of the transgene into the embryo can be accomplished by any means known in the art such as, for example, microinjection, electroporation, or lipofection. For example, the HSP70 transgene can be introduced into a mammal by microinjection of the construct into the pronuclei of fertilized mammalian egg(s) to cause one or more copies of the construct to be retained in the cells of the developing mammal(s). Following the introduction of the transgene construct into the fertilized egg, the egg may be incubated in vitro for varying amounts of time, or reimplanted into a surrogate host, or both. In vitro incubation to maturity is within the scope of this invention.

Transgenic offspring may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful in detecting the presence of the transgene product in the blood, as well as in evaluating the effect of the transgene on the levels of various types of blood cells and other blood constituents.

Utility

It is known that HSPS can be detected in all cells, prokaryotic and eukaryotic. Cells or multi-cell organisms respond to heat or other stresses by inducing or increasing the synthesis of HSPs. Increased levels of HSPs occur after heat stress, environmental stresses, infection, normal physiological processes and gene transfer. Based on the ability of HSPs to protect cells against various stressors, the transgenic pig of the invention highly expressing the HSPs has wide applications.

According to the invention, the transgenic pig of the invention can be used to detect environmental stressors associated with the production of HSPS. Previous studies indicated that transition series metals and sulfhydryl reagents induce the synthesis of HSP70 (Levinson et al., *Biochimica et Biophysica Acta,* 1980, 606, 170-180; Johnston et al., *The Journal of Biological Chemistry,* 1980, Vol. 255, No. 14, pp. 6975-6980). Thus, environmental stressors such as air, land or heavy metal pollution can be detected by assaying the production of HSPs in the transgenic pig of the invention.

According to the invention, the transgenic pig of the invention also can be used as an animal model close to human for illustrating the function of HSP in increasing cell survival and protecting cells from thermal injury in conditions such as sepsis, ischemia reperfusion injury, oxidant injury, atherosclerosis and aging.

According to the invention, the transgenic pig may be used as a xenograft source for example of xenograft organs, tissues or cells for transplantation. Xenografts of the invention can reduce rejection after transplantation, for example of xenograft organs such as kidney, liver, pancreas and lung; xenograft tissues such as skin, intestine, endocrine glands, islets, stem cells, bone marrow and vascular tissue; and xenograft cells such as embryo cell, sperm cell and ovum cell.

According to the invention, the transgenic pigs permit the production of HSPs in a large quantity, which is easily recoverable. For instance, HSP can be produced in the mammary gland of transgenic pigs and excreted in their milk. Milk is a biological fluid that can be easily collected, and has a relatively limited complexity and a low proteolytic activity. Given the above, HSP having biological activity can be mass-produced from the transgenic pig of the invention.

According to the invention, the transgenic pig has an improved meat quality and improved performance in growth and reproduction for the reason that the transgenic pig has an elevated expression of HSP, which can protect against heat stress. It is known that the growth, reproductive performance, and meat quality of pigs will be reduced when they are under heat stress. For example, Becker et al. indicated that the pigs under heat stress reduce the growth performance and their meat quality (Becker et al., *J. Anim. Sci.* 71:2375-2387). Wettemann et al. described the influence of elevated temperature on reproductive performance of boars (Wettemann et al., *J. Anim. Sci.* 42:664-669). Thus, the transgenic pig of the invention overexpressing HSP exhibits a superior growth, such as increased food intake and growth rate, a low backfat thickness, a better meat quality, and an increased reproductive performance.

The following examples are offered by way of illustration and not by way of limitation.

EXAMPLES

Example 1

The Production of a Transgenic Pig of the Invention

The transgenic pigs of the invention were generated using a chimeric transgene consisting of a porcine inducible HSP70.2 gene inserted into the vector pcDNA3.1/CT-GFP-TOP. Preparation of the DNA Fragments for Microinjection The porcine HSP70.2 gene was prepared from testis cDNA by reverse transcription-PCR with the following primers:

```
F5: 5'-AACATGGCGAAGAGCGTGGCC-3'    (SEQ ID NO:2)

R8: 5'-CCACCTCCTCGATGGTGGGG-3'    (SEQ ID NO:3)
```

The HSP70 expression vector was constructed using a CT-GFP Fusion TOPO Cloning Kit (Invitrogen, Carlsbad, Calif., USA), in accordance with the manufacturer's instructions. Each TOPO cloning reaction contains 100 ng of PCR product, 1 µl of pcDNA3.1/CT-GFP-TOPO, and judged total volume to 5 µl by sterile water. After the resulting solution was gently mixed and incubated for 5 minutes, 1 µl of the 6× TOPO Cloning Stop Solution was added immediately and then the solution was mixed for about 10 seconds at room temperature. A vial of One Shot cells was added to 2 µl of the TOPO Cloning mixture, and they were then mixed gently. After incubation on ice for 30 minutes, the cells were heat shocked at 42° C. for 30 seconds without shaking. The cells were immediately transferred to ice and incubated for 2 minutes. Two hundred fifty microliters of SOC medium under room temperature was added to the cells. Ten to fifty microliters of solution from each transformation were spread on a prewarmed LB plate containing 50 µg/ml ampicillin and incubated overnight at 37° C.

The pcDNA3.1/CT-GFP-TOPO construct places the HSP70.2 gene under the control of the human cytomegalovirus immediate-early enhancer and promoter. FIG. 1 shows a map of the hCMV/HSP70.2-GFP transgene. The coding region of the porcine inducible HSP70.2 gene and GFP gene is under the control of the human CMV immediate-early (hCMV-IE) enhancer and promoter. The chimeric gene is followed by the SV40 polyadenylation signal. The Nru I to Nsi I fragment was used to generate transgenic pigs. The chimeric transgene was cut out of the plasmid by Nru I and Nsi I digestion, purified, and used to generate transgenic pigs. The cut fragments were dissolved in 10 mM Tris-HCl, pH7.5, 0.1 mM EDTA to a final concentration of 2-4 µg/ml.

Animals and Treatment

Pure breed Duroc gilts at least seven and half months old were used. The animals were fed with 1.0 to 1.2 kg of commercial feed twice per day and water ad libitium. Sows in lactation were fed with lactation feed and water ad libitium. The transgenic piglets were weaned at 28 to 56 days.

All embryo donor and recipient gilts were synchronized by feeding Regumate (containing 0.4% altrenogest; 20 mg/day; Intervet, Boxmeer, Netherlands) mixed with commercial feed in the morning for 15 days, superovulated by injection of PMSG (1500-2000 IU, i.m., China Chem. And Pharm., Taiwan) at 24 hrs. after the last feeding of Regumate and injection of hCG (1250-1750 IU, i.m., China Chem. And Pharm., Taiwan) at 76 to 78 hrs. after the injection of PMSG, and mated by artificial insemination with pure breed Duroc boars' fresh-diluted semen at 24 to 36 hrs. after the injection of hCG.

At 54 to 56 hrs after the injection of hCG, the donor pigs were surgically operated to flush fertilized eggs from the fallopian tubes with 20 ml Dulbecco's-PBS (Gibco/BRL, USA) with 0.4% BSA (Fraction V, Sigma, USA) into a dish. Before the operation, pigs were fasted overnight, and were calmed by injection (i.m.) with 5 ml sterinil (2 mg/kg, Janssen Pharmaceutical, Belgium) and 10 ml atropine sulfate (90.04 mg/kg, China Chem. And Pharm., Taiwan). The pigs then were initially anaesthetized by injection of sodium pentobarbitone (10 mg/kg, Abbott Australasia Pty Ltd., Australia) into an ear vein. Anesthesia was maintained throughout the operation via a closed-circuit system using 4% halothene (ICI Ltd., USA) inhalation with oxygen gas.

Production of Transgenic Pigs

The DNAs used for injection were diluted with TE buffer (10 mM Tris-HCl, 0.1 mM EDTA, pH7.4) to 2 ng/µl for each HSP70 clone.

The fertilized eggs were centrifuged at 23,500× g for 8 min. at room temperature by centrifuge (Hettich EBA 12, Germany) to expose pronuclei. The pig embryos were micromanipulated using a Leica mechanical manipulator with a differential interference contrast inverted microscope (ZEISS Axiovert 135, Germany). The transgene was injected to the pronucleus of newly fertilized pig eggs or the nucleus of two-cell of pig embryos. After about 25 to 30 pig embryos were injected, the embryos were transferred into the fallopian tubes of recipient-synchronized sows as soon as possible.

Analysis of Transgene

After the pregnancy of the sow was complete and piglets were delivered, the ear tissue of live piglets or tail tissues of the stillborn piglets were taken to extract gnomic DNAs at the delivery day.

The transgenes were screened by PCR with primers

```
F8:          5'-GACGCCAACGGCATCCTGAAC-3'    (SEQ ID NO:4)
GFP-reverse: 5'-TAGAAGGCACAGTCGAGG-3'      (SEQ ID NO:5)
```

The PCR reaction was conducted as follows and the reaction products were analyzed by 2% agarose gel-electrophoresis.

As shown in Table II, two piglets carried the transgene as determined by PCR using primers F8 (SEQ ID NO:4) and GFP-reverse (SEQ ID NO:5). The transfer rate was 16.7%.

TABLE II

| No. of Embryos | No. of foster Embryos (%) | | No. of Pups (%) | |
| --- | --- | --- | --- | --- |
| Microinjected | Transferred | Delivered | Born/Analyzed | Tg |
| 181 | 8 | 4(50) | 12/12 | 2(16.7) |

Example 2

HSP Analysis of the Transgenic Pig

Protein Analysis in Transfected Cell

Figure 2:
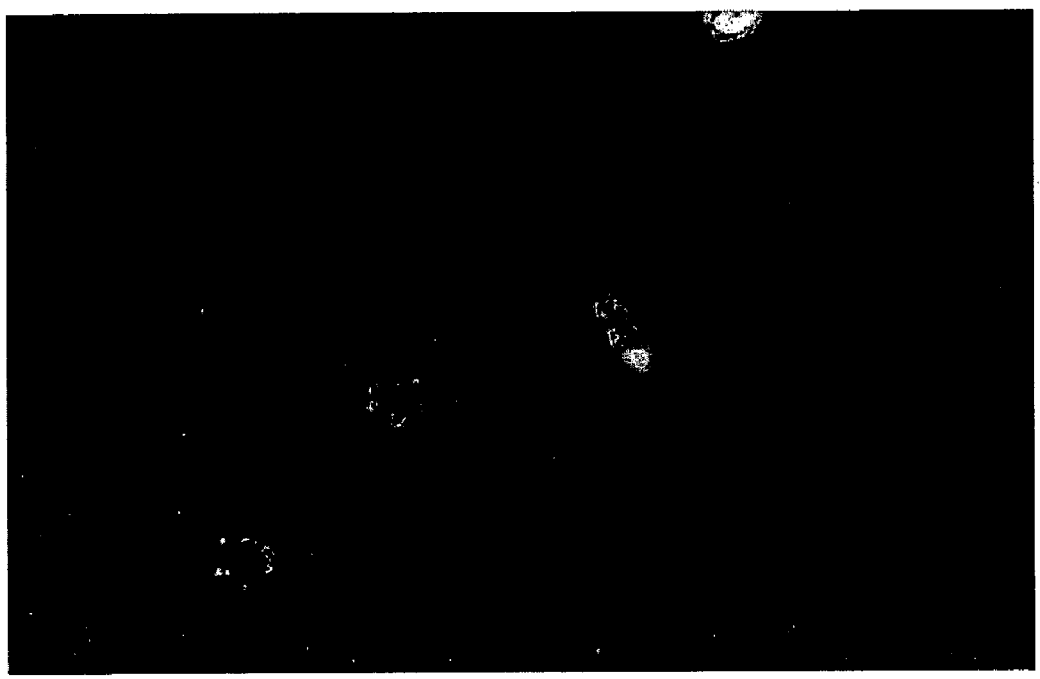
FIG. 2 shows the intracellular distribution of porcine HSP70.2-GFP expressed in monkey COS-7 cells analyzed by direct fluorescence.

Expression of the porcine HSP70.2-encoding gene in transfected COS-7 cells was first verified by observing green fluorescence directly from a HSP70.2-GFP fusion protein. Monkey kidney COS-7 cells were grown in Dulbecco's modified medium supplemented with 10% fetal bovine serum and appropriate antibiotics. Exponentially growing COS-7 cells were transfected with a plasmid containing the porcine gene for HSP70.2 using a SuperFect Transfection Reagent (Qiagen, Chatsworth, Calif., USA), in accordance with the manufacturer's instructions. Neomycin-resistant cells were selected in medium containing G418 (400 μg/ml), and colonies were isolated, trypsinized, and grown to confluent mono layers for further characterization. FIG. 2 shows the intracellular distribution of the porcine HSP70.2GFP gene product expressed in monkey COS-7 cells analyzed by direct fluorescence wherein the green fluorescence represents the HSP70.2-GFP fusion protein.

Protein Analysis in Transgenic Pig

Pigs underwent protein analysis to determine the expression of transgenic HSP-GFP. The tails or ears were taken at 3 days and 6 months of age and placed in lysis buffer on ice. The tissues were then homogenized using a polytron and placed directly on ice. The homogenized slurry was transferred to a clean tube and centrifuged at 12,000 rpm for 5 min at 4° C. The supernatant was aliquoted into sterile microcentrifuge tubes aliquoted samples were kept at −20° C. until used.

Total proteins were electrophoresed in 9% SDS-PAGE, transferred by electrophoresis to nitrocellulose filters and reacted with anti-HSP70 polyclonal antibody (Stressgen SPA-812) or with anti-GFP monoclonal antibody (Invitrogen). They then were incubated with an anti-rabbit 19G-alkaline phosphatase-conjugated secondary antibody. Specific antibody binding was detected using NBT/BCIP.

Figure 3A:
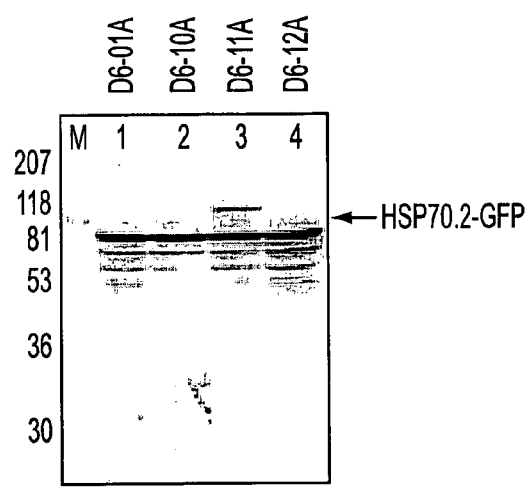
FIG. 3 shows a western blot of samples prepared from tail clips. The samples are probed with a polyclonal anti-HSP70 antibody (A) or a monoclonal anti-GFP antibody and anti-actin antibody (B).
Figure 3B:
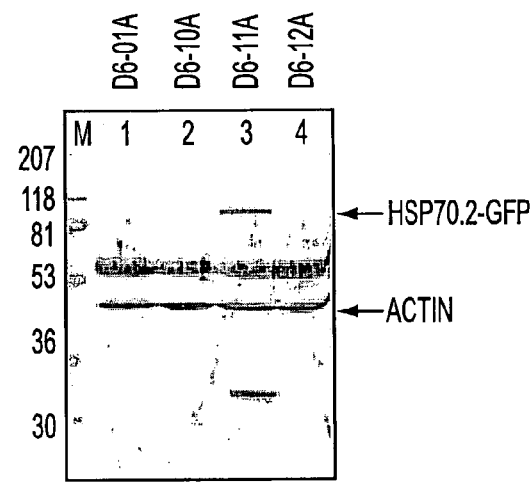

Expression of the porcine HSP70.2 in transgenic pigs was confirmed by immunoblot analysis using anti-HSP70 pAb (Stressgen SPA-812, specific against the inducible form). The tissue proteins separated by using 9% SDS-PAGE were detected via immunoblot analysis. A western blot of samples prepared from tail clips is shown in FIG. 3. The samples are probed with a polyclonal anti-HSP70 antibody (A) and a monoclonal anti-GFP antibody and anti-actin antibody (B). The additional 100-kDa polypeptide is the HSP70.2-GFP fusion protein.

Example 3

Viability of Cells with or without HSP70 Under Stress

Fibroblast Cell Culture from Piglet's Ear

Figure 4:
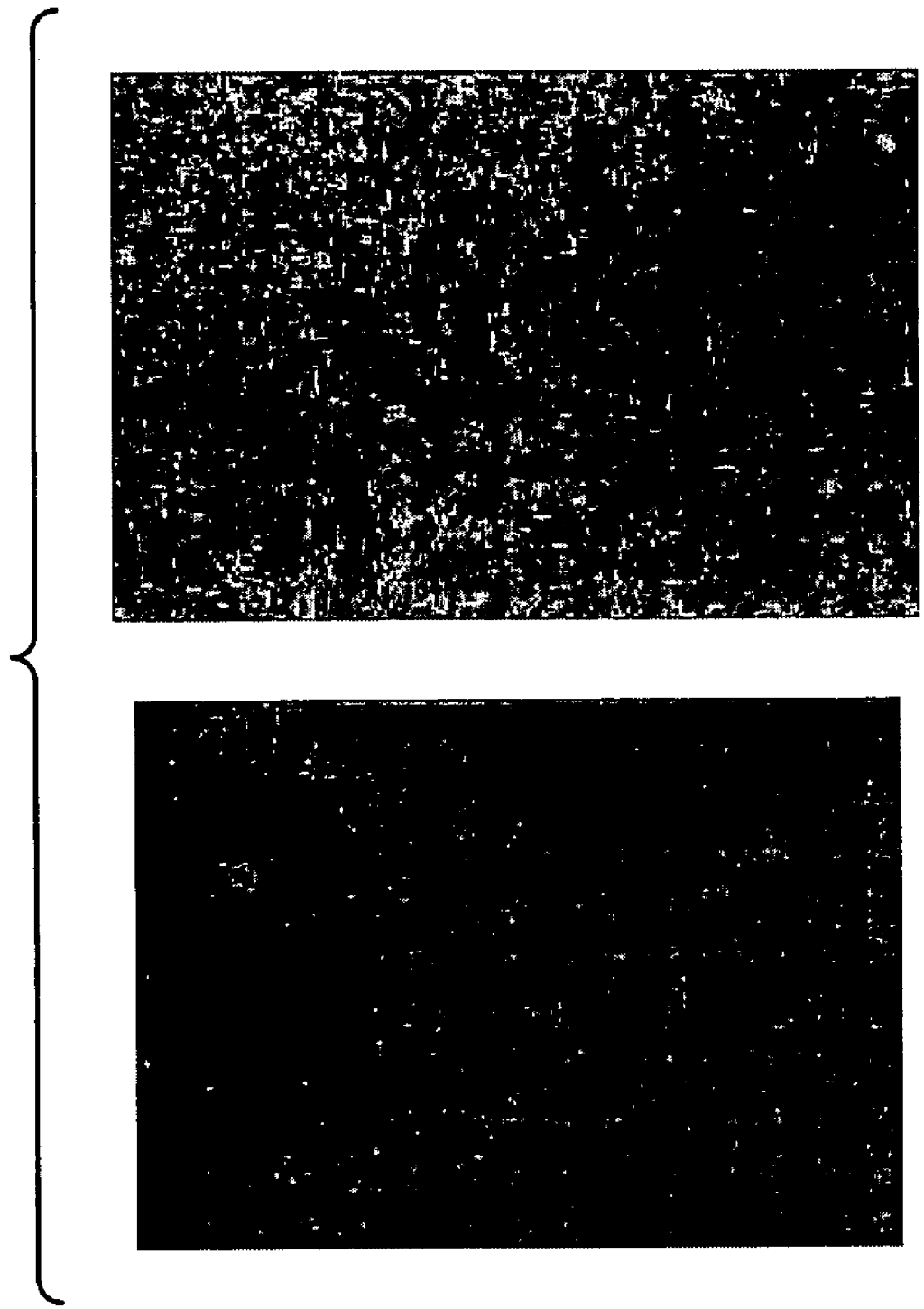
FIG. 4 shows green fluorescence in cultured primary fibroblast cells taken from transgenic pigs' ear.

Primary fibroblasts were isolated from the ears of the transgenic pigs at seven months old and were cultured. After dispase (Sigma) treatment. at 37° C. for 2 hrs, the ear tissues were immersed in 0.1% collagenase (Sigma) at 37° C. for another 2 hrs. The cells released to the suspension were collected by centrifuging at 800 rpm for 10 min and were subsequently cultured in a 25 mm flask. FIG. 4 shows green fluorescence in an assay performed on cultured fibroblast cells taken from transgenic pigs' ear which represents HSP70.

Heat Treatment and Cell Survival

Primary fibroblast cells were grown to 90% confluency and then treated with lethal heat shock at 45° C. for 3 hrs. in a water bath. Subsequent to this period, the media were removed to a centrifuge tube and the cells released to the media were collected by centrifuging at 800 rpm for 10 min. The cells still attached on the tissue culture plates were combined with those released to media as described. Cell viability was assessed by trypan blue exclusion as described by Riabowol et al, 1988, *Science*, 242(4877):433-436. All experiments were done at least three times and yielded consistent results.

Figure 5:
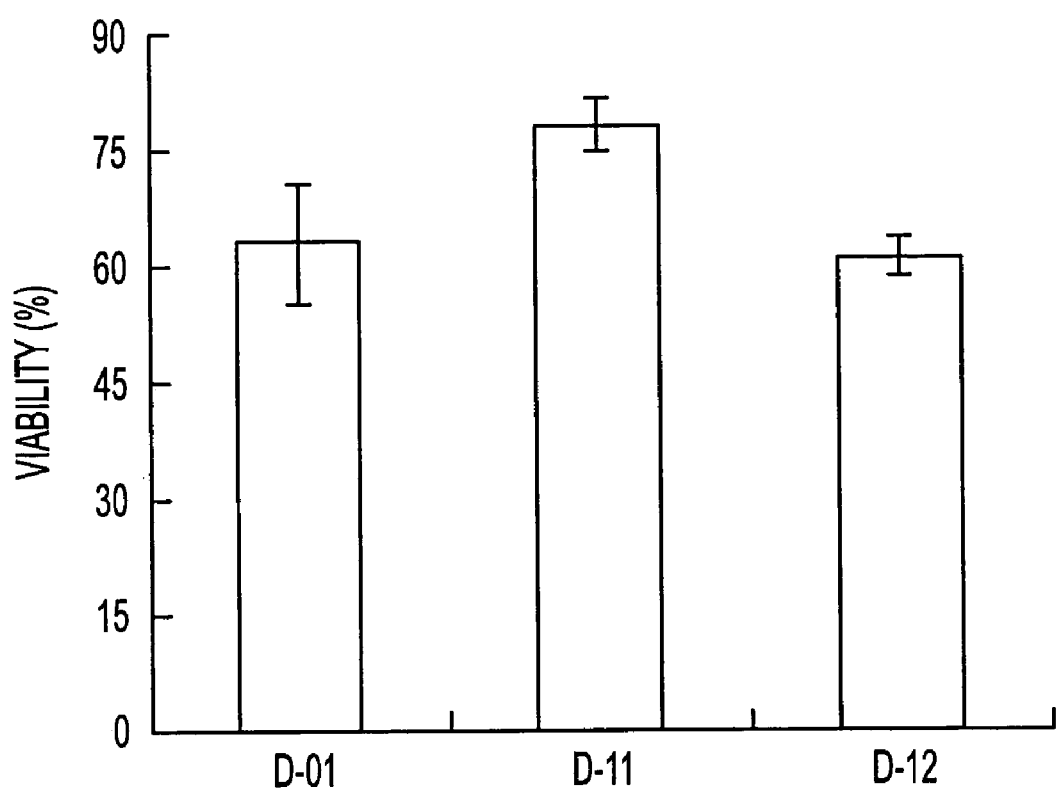
FIG. 5 shows cell survival after heat shock wherein D-01 represents non-transgenic pig and D-11 and D-12 represent transgenic pig.

The ability of experimental and control primary fibroblasts to survive the lethal heat treatment was examined. Primary fibroblasts of the transgenic pigs and non-transgenic pigs were subjected to an initial heat treatment. A trypan-blue exclusion assay (Riabowol et al 1988) and test for the ability to form colonies were used to estimate cell survival. Primary fibroblasts receiving a heat stress at 43° C. for 3 hrs., were tested for survival of the lethal heat challenge. Up to 75% of cells survive when cultured from transgenic animal overexpressing HSP70, whereas 60% of cells survive when cultured from non-transgenic animal (P=0.018). FIG. 5 shows cell survival after heat shock wherein D-01 represents non-transgenic pig and D-II and D-12 represent transgenic pigs. The result evidenced that HSP70 protein was at least partially responsible for protection of cells against a lethal heat treatment.

What is claimed is:

1. A transgene comprising a nucleic acid encoding a pig HSP70 protein, wherein said nucleic acid is set forth in SEQ ID NO:1.

2. An expression vector containing the transgene as claimed in claim 1.

* * * * *

SEQUENCE LISTING

<160> NUMBER OF SEQ ID NOS: 5

<210> SEQ ID NO 1
<211> LENGTH: 2310
<212> TYPE: DNA
<213> ORGANISM: procine

<400> SEQUENCE: 1

| | | | | | |
|---|---|---|---|---|---|
| acaactccgc | cccattgacg | caaatgggcg | gtaggcgtgt | acggtgggag | gtctatataa | 60 |
| gcagagctct | ctggctaact | agagaaccca | ctgcttactg | gcttatcgaa | attaatacga | 120 |
| ctcactatag | ggagacccaa | gctggctagt | taagcttggt | accgagctcg | gatccactag | 180 |
| tccagtgtgg | tggaattgcc | cttaacatgg | cgaagagcgt | ggccatcggc | atcgacctgg | 240 |
| gcaccacgta | ctcgtgcgtg | ggggtgttcc | agcacggcaa | ggtggagatc | atcgccaacg | 300 |
| accaggcaa | ccgcactacc | cccagctacg | tggccttcac | ggacaccgag | cggctgatcg | 360 |
| gcgatgcggc | caagaaccag | gtggcgctga | acccgcagaa | cacggtgttt | gacgcgaagc | 420 |
| ggctgatcgg | gcgcaagttc | ggcgaccccg | tggtgcaggc | ggacatgaag | cactggccct | 480 |
| tccgggtgat | caacgacggg | gacaagccca | aggtgcaggt | gagctacaag | ggcgagacca | 540 |
| aggcgttcta | cccggaggag | atctcgtcga | tggtgctgac | caagatgaag | gagatcgccg | 600 |
| aggcgtacct | gggccacccg | gtgagcaacg | cggtgatcac | ggtgccggcc | tacttcaacg | 660 |
| actcgcagcg | gcaggccacc | aaggatgcgg | gggtgatcgc | ggggctgaac | gtgctgcgga | 720 |
| tcatcaacga | gcccacggcg | gcggccatcg | cctacggcct | ggacaggacg | ggcaaggggg | 780 |
| agcgcaacgt | gctgatcttc | gacctgggcg | ggggcacgtt | cgacgtgtcc | atcctgacga | 840 |
| tcgacgacgg | catcttcgag | gtgaaggcca | cggcggggga | cacgcacctg | gcggcgagg | 900 |
| acttcgacaa | caggctggtg | aaccacttcg | tggaggagtt | caagaggaag | cacaagaagg | 960 |
| acatcagcca | gaacaagcgg | gcggtgaggc | ggctgcgcac | ggcctgcgag | cgggccaaga | 1020 |
| ggaccctgtc | gtccagcacg | caggccagcc | tggagatcga | ctccctgttc | gagggcatcg | 1080 |
| acttctacac | gtccatcacc | cgggcgcgct | tcgaggagct | gtgctcggac | ctgttccgca | 1140 |
| gcaccctgga | gccggtggag | aaggctctgc | gcgacgcgaa | gctggacaag | ggccagattc | 1200 |
| acgacctggt | gctggtgggg | ggctcgacgc | gcatccccaa | ggtgcagaag | ctgctgcagg | 1260 |
| acttcttcaa | cgggcgcgac | ctcaacaaga | gcatcaaccc | ggacgaggcg | gtggcgtatg | 1320 |
| gggcggcggt | gcaggcggcc | atcctgatgg | gcgacaagtc | ggagaacgtg | caggacctgc | 1380 |
| tgctgctgga | cgtggccccg | ctgtcgctgg | ggctggagac | ggccggcggc | gtgatgacgg | 1440 |
| cgctgatcaa | gcgcaactcc | accatccccca | ccaagcagac | gcagatcttc | accacgtact | 1500 |
| cggacaacca | gccgggcgtg | ctgatccagg | tgtacgaggg | cgagagggcc | atgacgcggg | 1560 |
| acaacaacct | gctgggcgc | ttcgagctga | gcggcatccc | gccggccccg | cgggggtgc | 1620 |
| cccagatcga | ggtgacctc | gacatcgacg | ccaacggcat | cctgaacgtc | acggcgacgg | 1680 |
| acaagagcac | gggcaaggcc | aacaagatca | ccatcaccaa | cgacaagggc | cggctgagca | 1740 |
| aggaggagat | cgagcgcatg | gtgcaggagg | cggagaagta | caaagcggag | gacgagatcc | 1800 |
| agcgcgagg | ggtgtcggcc | aagaacgcgc | tggagtcgta | cgccttcaac | atgaagagcg | 1860 |
| ccgtggagga | tgagggctc | aagggcaaga | tcagcgaggc | ggacaagaag | aaggtgctgg | 1920 |
| acaagtgtca | ggaggtgatt | tcctggctgg | acgccaacac | gctggccgag | aaggacgagt | 1980 |
| ttgagcacaa | gaggaaggag | ctggagcagg | tgtgtaaccc | catcatcagc | ggactgtacc | 2040 |

-continued

```
agggggcggg tggccccggg gctggcggct ttggggctca ggcccccaaa gggggctctg    2100
ggtctggccc caccatcgag gaggtggaag ggcaattctg cagatatcca gcacagtggc    2160
ggccgctcga gtctagaatg gctagcaaag gagaagaact tttcactgga gttgtcccaa    2220
ttcttgttga attagatggt gatgttaatg ggcacaaatt ttctgtcagt ggagagggtg    2280
aaggtgatgc tacatacgga aagcttaccc                                     2310
```

<210> SEQ ID NO 2
<211> LENGTH: 21
<212> TYPE: DNA
<213> ORGANISM: Artificial Sequence
<220> FEATURE:
<223> OTHER INFORMATION: Primer to screen a procine testis cDNA library

<400> SEQUENCE: 2
aacatggcga agagcgtggc c         21

<210> SEQ ID NO 3
<211> LENGTH: 20
<212> TYPE: DNA
<213> ORGANISM: Artificial Sequence
<220> FEATURE:
<223> OTHER INFORMATION: Primer to screen a procine testis cDNA library

<400> SEQUENCE: 3
ccacctcctc gatggtgggg         20

<210> SEQ ID NO 4
<211> LENGTH: 21
<212> TYPE: DNA
<213> ORGANISM: Artificial Sequence
<220> FEATURE:
<223> OTHER INFORMATION: Primer to screen a porcine genomic DNA library

<400> SEQUENCE: 4
gacgccaacg gcatcctgaa c         21

<210> SEQ ID NO 5
<211> LENGTH: 18
<212> TYPE: DNA
<213> ORGANISM: Artificial Sequence
<220> FEATURE:
<223> OTHER INFORMATION: Primer to screen a porcine genomic DNA library

<400> SEQUENCE: 5
tagaaggcac agtcgagg         18